United States Patent
Selbach et al.

(10) Patent No.: US 9,458,083 B2
(45) Date of Patent: Oct. 4, 2016

(54) METHOD FOR HYDROLYSING ACETONE CYANOHYDRIN

(71) Applicants: Arndt Selbach, Erftstadt (DE); Lorenza Sartorelli, Ober-Ramstadt (DE); Andreas Perl, Bobenheim-Roxheim (DE); Joachim Deinken, Eschborn (DE); Stefanie Sohnemann, Overath (DE); Norbert Mnich, Erlensee (DE); Matthias Groemping, Darmstadt (DE); Udo Gropp, Bad Endorf (DE); Thomas Mertz, Bensheim (DE)

(72) Inventors: Arndt Selbach, Erftstadt (DE); Lorenza Sartorelli, Ober-Ramstadt (DE); Andreas Perl, Bobenheim-Roxheim (DE); Joachim Deinken, Eschborn (DE); Stefanie Sohnemann, Overath (DE); Norbert Mnich, Erlensee (DE); Matthias Groemping, Darmstadt (DE); Udo Gropp, Bad Endorf (DE); Thomas Mertz, Bensheim (DE)

(73) Assignee: EVONIK ROEHM GmbH, Darmstadt (DE)

( * ) Notice: Subject to any disclaimer, the term of this patent is extended or adjusted under 35 U.S.C. 154(b) by 108 days.

(21) Appl. No.: 14/384,273

(22) PCT Filed: Mar. 6, 2013

(86) PCT No.: PCT/EP2013/054486
§ 371 (c)(1),
(2) Date: Sep. 10, 2014

(87) PCT Pub. No.: WO2013/143812
PCT Pub. Date: Oct. 3, 2013

(65) Prior Publication Data
US 2015/0045577 A1    Feb. 12, 2015

(30) Foreign Application Priority Data

Mar. 30, 2012    (DE) .................. 10 2012 205 257

(51) Int. Cl.
*B01J 19/18* (2006.01)
*B01J 19/24* (2006.01)
*C07C 231/06* (2006.01)
*C07C 253/30* (2006.01)
*C07C 51/06* (2006.01)
*C07C 51/08* (2006.01)
*C07C 51/377* (2006.01)
*C07C 67/22* (2006.01)
*B01J 19/00* (2006.01)
*B01J 4/00* (2006.01)

(52) U.S. Cl.
CPC ............ *C07C 67/22* (2013.01); *B01J 19/1868* (2013.01); *B01J 19/2415* (2013.01); *C07C 51/06* (2013.01); *C07C 51/08* (2013.01); *C07C 51/377* (2013.01); *C07C 231/06* (2013.01); *C07C 253/30* (2013.01); *B01J 4/008* (2013.01); *B01J 19/0013* (2013.01); *B01J 2219/00033* (2013.01); *B01J 2219/30261* (2013.01); *B01J 2219/30265* (2013.01)

(58) Field of Classification Search
CPC ............. B01J 19/1868; B01J 19/2415; B01J 19/0013; B01J 2219/00033; B01J 2219/30261; B01J 2219/30265; B01J 4/008; C07C 231/06; C07C 253/30; C07C 51/06; C07C 51/08; C07C 51/377; C07C 67/22
See application file for complete search history.

(56) References Cited

U.S. PATENT DOCUMENTS

| 3,921,711 A * | 11/1975 | Westbrock | F28F 13/08 122/367.4 |
| 7,582,790 B2 * | 9/2009 | Schladenhauffen | C07C 51/06 558/451 |
| 2009/0082587 A1 | 3/2009 | Schladenhauffen et al. | |
| 2013/0211140 A1 | 8/2013 | Sartorelli et al. | |

FOREIGN PATENT DOCUMENTS

| CN | 102395422 A | 3/2012 |
| WO | WO2010121882 | * 10/2010 |

OTHER PUBLICATIONS

Combined Office Action and Search Report issued Aug. 10, 2015 in Chinese Patent Application No. 201380017252.9 (with English language translation).
Ma Xiaoming, et al., "Shell-and-tube heat exchanger", Cataloguing in Publication (CIP) Data, China Petrochemical Press, 1st edition, 1st printing, Jan. 2010, pp. 180-182 (with English language translation).
International Search Report Issued Jun. 28, 2013 in PCT/EP13/054486 Filed Mar. 6, 2013.

* cited by examiner

*Primary Examiner* — Paul A Zucker
*Assistant Examiner* — Mark Luderer
(74) *Attorney, Agent, or Firm* — Oblon, McClelland, Maier & Neustadt, L.L.P.

(57) ABSTRACT

The present invention relates to a process for hydrolysis of acetone cyanohydrin (ACH) by means of sulphuric acid within the ACH sulpho process for preparation of methacrylic acid (MAA) or methyl methacrylate (MMA).

7 Claims, 3 Drawing Sheets

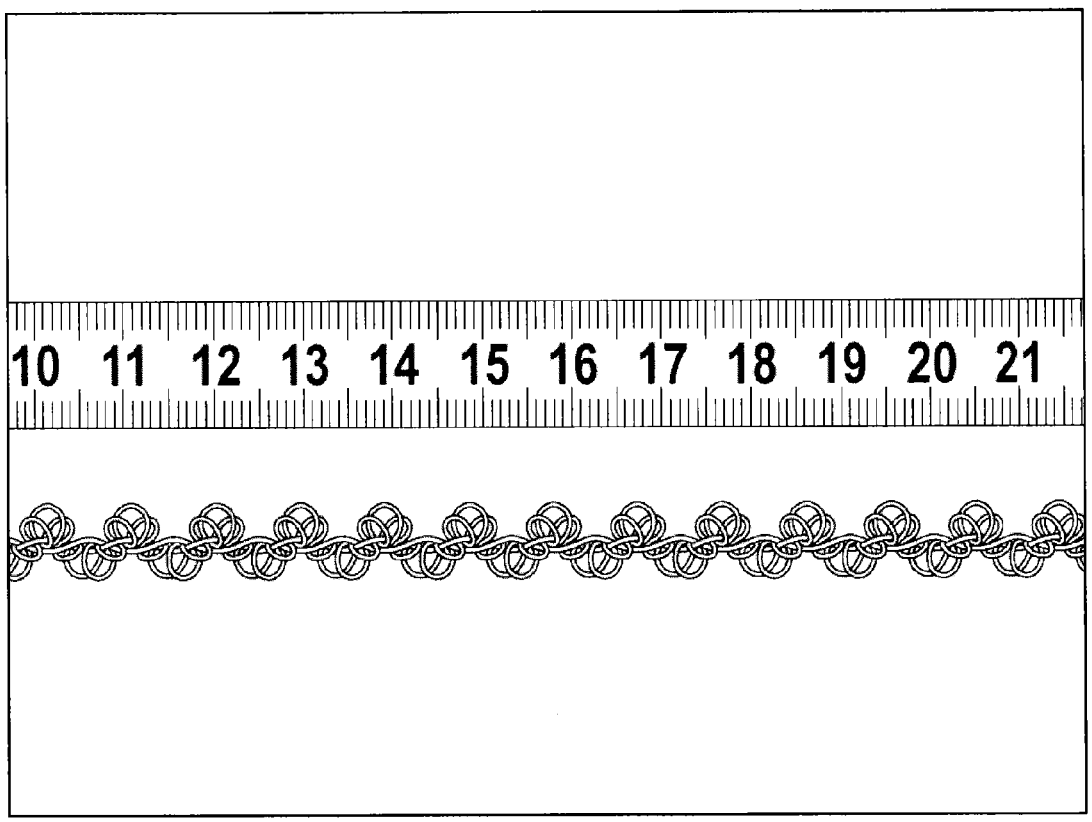
Fig. 1: Turbulator

Fig. 2 Flow diagram for comparative examples 1-4
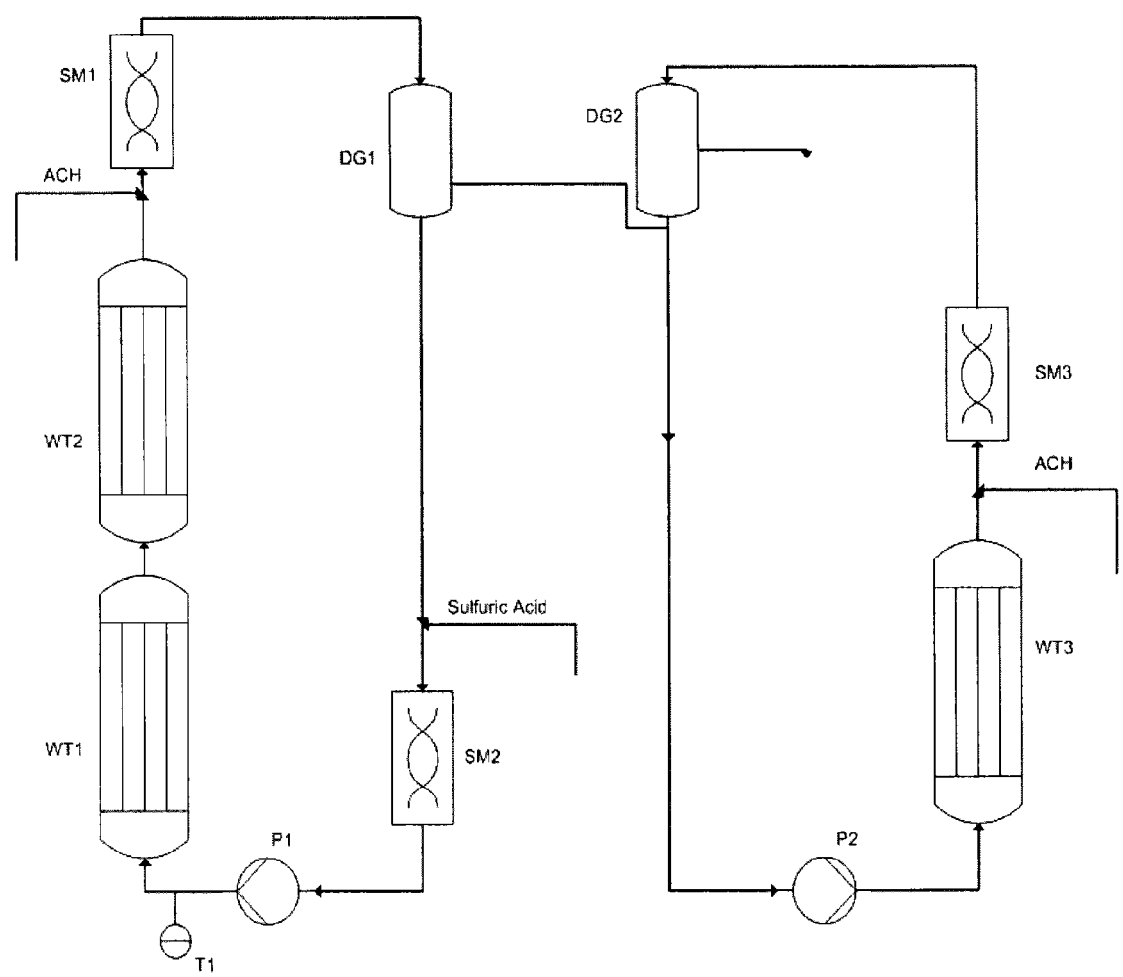

Fig. 3: Flow diagram for examples 1-4
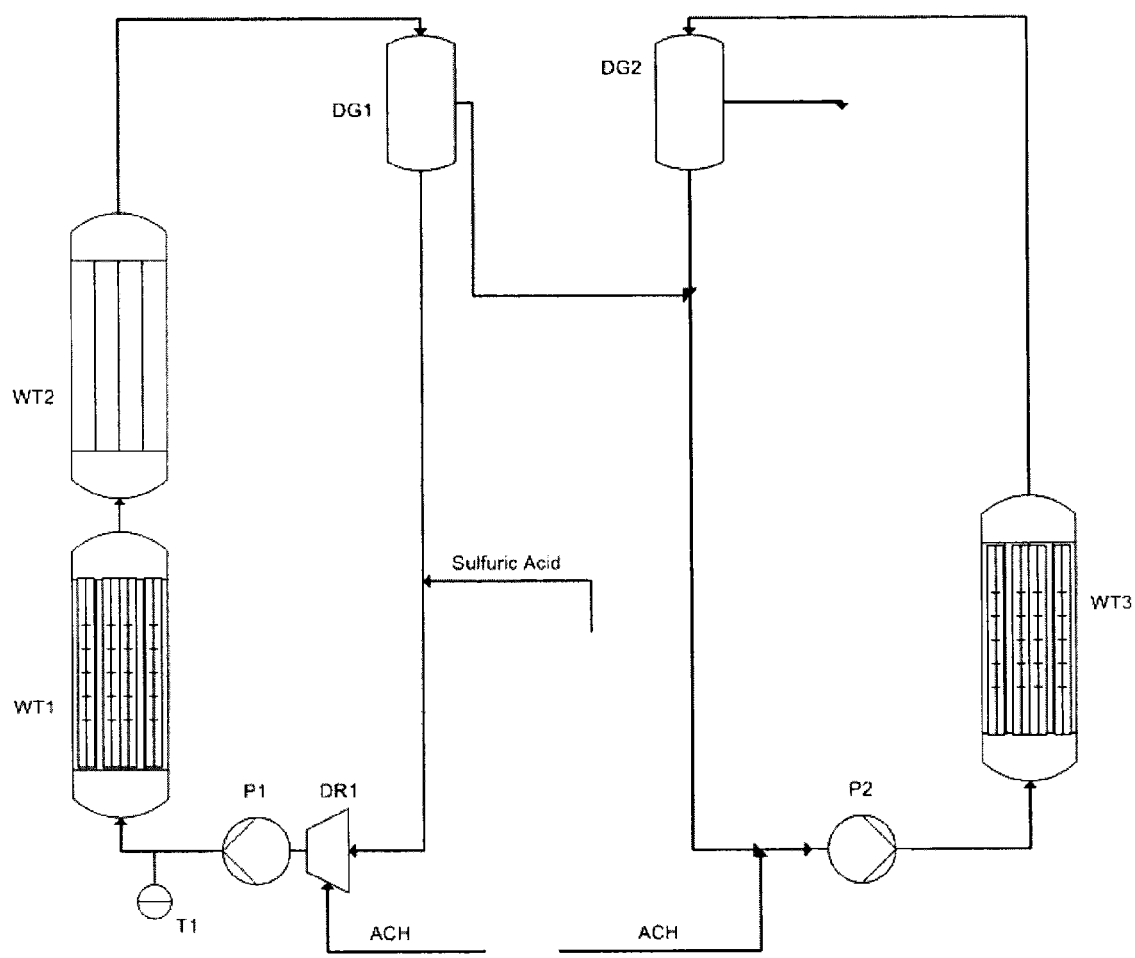

METHOD FOR HYDROLYSING ACETONE CYANOHYDRIN

The present invention relates to a process for hydrolysis of acetone cyanohydrin (ACH) by means of sulphuric acid within the ACH sulpho process for preparation of methacrylic acid (MAA) or methyl methacrylate (MMA).

The preparation of MAA or MMA by the ACH sulpho process is common knowledge and is described, for example, in EP 2054370. Proceeding from hydrogen cyanide and acetone, ACH is prepared in a first step, and is then converted to methacrylamide (MAAm). These steps are described, inter alia, in U.S. Pat. No. 7,253,307, EP 1666451 or EP 2007059092. For preparation of MAAm, acetone cyanohydrin is subjected to a hydrolysis. This forms the desired MAAm at various temperature levels after a series of reactions. The conversion is brought about in a manner known to those skilled in the art by a reaction between concentrated sulphuric acid and ACH. The reaction is exothermic, and so heat of reaction is advantageously removed from the system.

The reaction can be performed in a batchwise process or in continuous processes. The latter has been found to be advantageous in many cases. If the reaction is performed within a continuous process, the use of loop reactors has been found to be useful. Loop reactors are known in the specialist field. These may especially be configured in the form of tubular reactors with recycling. The reaction can be effected, for example, in just one loop reactor. However, it may be advantageous when the reaction is performed in a cascade of two or more loop reactors.

A suitable loop reactor has, in the context of the process described, one or more feed points for ACH, one or more feed points for concentrated sulphuric acid, one or more gas separators, one or more heat exchangers and one or more mixers. The loop reactor may comprise further constituents such as conveying means, pumps, control elements, etc.

The hydrolysis of ACH with sulphuric acid is exothermic. In parallel to the main reaction, several side reactions take place, which lead to lowering of the yield.

In the preferred temperature range, the decomposition of ACH, likewise an exothermic and rapid reaction, plays a major role. The heat of reaction which occurs in the course of the reaction, however, has to be at least substantially removed from the system, since the yield falls with increasing operating temperature and rising residence time. In principle, it is possible to achieve rapid and comprehensive removal of the heat of reaction with appropriate heat exchangers. However, it may also be disadvantageous to cool the mixture too much prior to the metered addition of ACH, since high turbulence is needed both for mixing and for efficient heat removal. Since the viscosity of the reaction mixture rises significantly with falling temperature, there is correspondingly a fall in flow turbulence, in some cases down to the laminar range, which leads to less efficient heat removal in the heat exchanger and slower and less homogeneous mixing in the metered addition of ACH. What is required is rapid mixing of ACH and reaction mixture, since the ACH is to react before it is decomposed due to heating.

U.S. Pat. No. 7,582,790, for example, claims loop reactors with various internal mixing units, which may consist of static mixers, orifice plates, venturis, jet mixers, eductors, perforated plates, spargers, agitators, rotary mixers, high-velocity circulation loops or spray nozzles. All these mixing elements have the common disadvantage that they significantly increase flow resistance in the loop reactor and lead to considerable pressure drops. The latter cause a reduced flow rate and less effective heat exchange, which leads to yield losses owing to temperature peaks in this thermally sensitive reaction. Moreover, the mixing of the reaction components take place in mixing units arranged outside the heat exchangers.

It is therefore an object of the present invention to eliminate or at least to minimize the above-described disadvantages.

This object is achieved by a process for hydrolysis of ACH by means of sulphuric acid as a precursor for preparation of MAA or MMA in a loop reactor, characterized in that (a) at least one of the heat exchangers present in the loop reactor is equipped with turbulators and (b) at least one of the reaction components is fed into the loop reactor by means of a metering ring.

The inventive turbulators are described and thus disclosed in EP 061154. Since they are installed into the tubes of a heat exchanger, they have the advantage primarily of enabling good heat exchange, since they reduce the tendency to form a laminar flow. The use of these turbulators is described, for example, in WO 2007/075064 for a heterogeneous gas phase oxidation. It was surprising to the inventors that these turbulators, in spite of their physically simple configuration (see FIG. 1), in the present complex triphasic mixture with relatively high viscosity, still ensure improved heat exchange with simultaneously low pressure drop.

According to the invention, as described in EP 061154, the turbulators are installed into the reaction medium-conducting tubes of a shell-and-tube heat exchanger. At least 50-70% of the tubes, preferably 70-90% and more preferably 100% of the tubes are equipped with the turbulators. Turbulators of this kind are commercially available, for example, from Cal Gavin, Alcester, GB, under the "hiTRAN Thermal Systems" name. The number of turns per metre is 100-1200 turns/m, preferably 300-900 turns/m, more preferably 500-750 turns/m.

The length of the turbulators depends on the length of the tubes in the shell-and-tube heat exchangers used in each case. The turbulators should cover the entire length of the heat exchanger tubes.

As well as these thus defined turbulators, it is also possible to install other articles which obstruct the tube opening of the shell-and-tube heat exchanger, for example corkscrew-like or pipebrush-like structures and helically wound metal tapes of suitable width. The aim of these internals in all cases is to prevent laminar flow at the tube surface and simultaneously to build up only a minimum pressure drop.

The heat exchanger thus modified can in principle be positioned anywhere in the loop reactor, but it is preferably positioned downstream of the metered addition of sulphuric acid and of ACH in flow direction.

The inventive metering rings are described and thus disclosed in EP 2421637. In the use described therein in the present ACH hydrolysis by means of sulphuric acid, however, the starting point is merely the prior art with presence of static mixers.

The inventive metering ring may have various embodiments. For example, many small metering points can be introduced into the ring, or few large metering points. The metering points may also project into the interior of the tube of the loop reactor via small tubes, in particular embodiments also small tubes of varying length. This particular positioning of the metered addition at points removed from the tube wall positions the reactants such that optimal mixing is effected in the subsequent turbulences within the delivery pump. The small metering tubes which project into the tube diameter of the loop reactor may assume various angles to the tube wall, preferably an angle other than 90°, more preferably inclined in flow direction. The effect of this is that the reactant is introduced in a controlled manner into the inner regions of the tube flow and is not just distributed along the tube wall; the latter has an adverse effect on rapid and intensive mixing through the turbulences within the delivery pump.

According to the metering task, the metering ring may be cooled or heated. Here lies a further advantage of the external ring which is not heated by the surrounding medium, in contrast to a metering probe which necessarily projects into the tube. A particular embodiment is a metering ring in which the metered addition is effected under elevated pressure. The device may assume any suitable three-dimensional shape, and is preferably constructed in ring form. It is also possible here to use double or multiple rings.

The reactants can be introduced into the tubular reactor by means of a pump. To avoid maintenance-related operation shutdowns, it is also possible to provide two or more pumps which may be connected in parallel. The mixing of the reactants with a metering ring can appropriately be effected upstream of the pumps viewed in flow direction, i.e. on the pump suction side. The metering ring may, however, also be part of the pump and be integrated into the pump housing.

The components of the plant which come into contact with corrosive substances, especially the tubular reactor, the pumps, phase separator, metering ring and heat exchanger and the turbulators installed therein, are formed from suitable materials, for example an acid-resistant metal, for example zirconium, tantalum, titanium or stainless steel, or a coated metal having, for example, an enamel layer or a zircon layer. In addition, it is also possible to use polymers, for example PTFE-sheathed components, graphitized components or workpieces made from graphite, especially in pumps.

In one configuration of the process, a portion, preferably about two thirds to about three quarters, of the volume flow from a stream of ACH is introduced into a first loop reactor. Preferably, a first loop reactor has one or more heat exchangers with turbulators installed into at least one, one or more pumps, and one or more gas separators. The circulation flow rates passing through the first loop reactor are preferably in the range of 50-650 m$^3$/h, more preferably within a range of 100-500 m$^3$/h and additionally preferably within a range of 150-450 m$^3$/h. In an at least one further loop reactor following downstream of the first loop reactor, the circulation flow rates are preferably within a range of 40-650 m$^3$/h, more preferably within a range of 50-500 m$^3$/h and additionally preferably within a range of about 60-350 m$^3$/h.

In addition, a preferred temperature difference over the heat exchanger is about 1-20° C., more preferably about 2-7° C.

The feed of the ACH, according to the invention via a metering ring, into the loop reactor may in principle be effected at any point. However, it has been found to be advantageous when the feed is effected directly on the suction side of a pump. Thus, the highly turbulent flow in the pump housing is utilized for mixing of the reactants, and thus a conveying machine is utilized simultaneously as an additional mixing machine. The feed of the sulphuric acid is advantageously effected upstream of the addition of ACH. Otherwise, however, it is likewise possible to introduce the sulphuric acid into the loop reactor at any point.

The ratio of the reactants in the loop reactor is controlled such that an excess of sulphuric acid is present. The excess of sulphuric acid is, based on the molar ratio of the ingredients, about 1.8:1 to about 3:1 in the first loop reactor and about 1.1:1 to about 2:1 in the last loop reactor.

In some cases, it has been found to be advantageous to conduct the reaction in the loop reactor with such an excess of sulphuric acid. The sulphuric acid can serve here, for example, as a solvent and keep the viscosity of the reaction mixture low, as a result of which a more rapid removal of heat of reaction and a lower temperature of the reaction mixture can be ensured. This can entail distinct yield advantages. The temperature in the reaction mixture is about 85-150° C.

The heat removal is ensured by one or more heat exchangers in the loop reactor. At least one of these is equipped with the inventive turbulators. It has been found to be advantageous when the heat exchangers have a suitable sensor system for adjustment of the cooling performance in order to prevent excessive cooling of the reaction mixture for the reasons mentioned above. For example, it may be advantageous to measure the heat transfer in the heat exchanger(s) intermittently or continuously and to adjust the cooling performance of the heat exchangers thereto.

This can be accomplished, for example, by means of the coolant itself. It is also equally possible to achieve corresponding heating of the reaction mixture through appropriate variation of the addition of the reactants and through the generation of more heat of reaction. A combination of both options is also conceivable.

The loop reactor preferably additionally has at least one gas separator. The gas separator can be used firstly to withdraw product formed continuously from the loop reactor. Secondly, gases formed in the course of the reaction can thus be removed from the reaction space. The gas formed is mainly carbon monoxide. The product withdrawn from the loop reactor is preferably transferred into a second loop reactor. The reaction mixture comprising sulphuric acid and methacrylamide, as obtained through the reaction in the first loop reactor, is reacted in this second loop reactor with the remaining substream of ACH. In this case, the excess of sulphuric acid from the first loop reactor, or at least a portion of the excess sulphuric acid, reacts with the ACH to further form sulphoxyisobutyramide (SIBA). The performance of the reaction in two or more loop reactors has the advantage that the pumpability of the reaction mixture and hence the heat transfer and ultimately the yield are improved owing to the sulphuric acid excess in the first loop reactor. Again, at least one heat exchanger and at least one gas separator are arranged in the second loop reactor. The second ACH substream metered in here can likewise be metered in by means of a metering ring. At least one of the heat exchangers in the second loop reactor too is preferably equipped with turbulators. The reaction temperature in the second loop reactor is likewise 90-120° C.

Tab. 1 shows the experimental results. Example 1 and comparative example 1 were run at a moderate ACH load, low molar sulphuric acid to ACH ratio and moderate temperature level in circuit 1, and experiment series 2 likewise at moderate ACH load, but at moderate molar ratio and high temperature level. Experiment series 3 likewise exhibits moderate ACH load and moderate molar ratio, but the lowest temperature level. Finally, experiment series 4 was conducted at maximum ACH load, highest molar ratio and highest temperature level. In all experiment series, the temperature in the second circuit, measured beyond the heat exchanger WT3, was held at approx. 112° C.

TABLE 1

| | Process parameters and yields | | | | | | | |
|---|---|---|---|---|---|---|---|---|
| | ACH [kg/h] | $H_2SO_4$ [kg/h] | T1 [° C.] | Overall MR | Stage 1 MR | Yield [%] | | Yield [%] |
| Example 1 | 4500 | 7255 | 101.8 | 1.41 | 2.2 | 92.2 | Comparative example 1 | 90.5 |
| Example 2 | 4201 | 7013 | 107.1 | 1.46 | 2.2 | 93.2 | Comparative example 2 | 90.0 |
| Example 3 | 4200 | 7013 | 95.4 | 1.46 | 2.2 | 93.4 | Comparative example 3 | 90.4 |
| Example 4 | 6001 | 10364 | 107.1 | 1.51 | 1.8 | 93.3 | Comparative example 4 | 92.1 |

The problem of pumpability of the reaction mixture, of heat transfer and of a minimum reaction temperature exists just as much in every further loop reactor as in the first. Therefore, the heat exchanger in the second loop reactor advantageously also has a corresponding sensor system for control of the cooling performance.

The examples which follow are intended to describe but in no way to limit the invention.

Comparative examples 1-4 relating to the prior art were run in a plant as shown in the flow diagram FIG. 2, and inventive examples 1-4 analogously as shown in FIG. 3. Tab. 1 lists the respective process parameters and the corresponding yields.

FIG. 2 shows a two-stage loop reactor. About two thirds of the total amount of ACH is metered into the first circuit upstream of the static mixer SM1. Thereafter, the reaction solution passes through the degassing vessel DG1. Upstream of the static mixer SM2, the total amount of concentrated sulphuric acid is added. The pump P1 conveys the reaction solution through two shell-and-tube heat exchangers WT1 and WT2. At the temperature measurement point T1, the temperature of the first circuit is measured. The reaction solution is transferred from the degassing vessel DG1 into the second circuit of the loop reactor. The pump P2 conveys the reaction solution through a third shell-and-tube heat exchanger WT3. Thereafter, the remaining amount of ACH is metered in upstream of the static mixer SM3. The reaction solution is finally removed from the second degassing vessel DG2 into the next processing stage.

FIG. 3 shows the same construction in principle. However, all static mixers have been removed. ACH is metered in in the first circuit immediately upstream of the pump P1 via the inventive metering ring DR1. In the heat exchanger WT1, inventive turbulators having a number of turns of 550 turns/m and a length of 2 m are installed, and, in the heat exchanger WT3, those having a number of turns of 700 turns/m and a length of 1 m are installed.

As can be seen from Tab. 1, the yields in the inventive examples are 2-3% higher than in the comparative examples.

Labels for the Figures

| | |
|---|---|
| SM1, SM2, SM3 | Static mixers |
| WT1, WT2, WT3 | Shell-and-tube heat exchangers |
| P1, P2 | Pumps |
| DR1 | Metering ring |
| DG1, DG2 | Degassing vessels |

The invention claimed is:

1. A process for hydrolysis of acetocyanohydrin, the process comprising:
   preparing methyl methacrylate in a loop reactor by using sulphuric acid as a precursor,
   wherein
   at least one heat exchanger present in the loop reactor is equipped with turbulators,
   at least one reaction component is fed into the loop reactor via a metering ring, which is installed externally and immediately upstream of a pump with a pump housing in the loop reactor,
   the at least one heat exchanger equipped with turbulators is positioned downstream of a metered addition of sulphuric acid and of acetocyanohydrin in flow direction, and
   the turbulators are turbulators with 100-1200 turns/m.

2. The process according to claim 1, wherein the metering ring is integrated into the pump housing.

3. The process according to claim 1, wherein corkscrew or piperbrush structures are installed as turbulators into the at least one heat exchanger.

4. The process according to claim 1, wherein helically wound metal tapes are used on turbulators in the loop reactor.

5. The process according to claim 1, wherein
   the at least one heat exchanger is a shell-and-tube heat exchanger, and at least 50-70% of tubes of the shell-and-tube heat exchanger are equipped with turbulators.

6. The process according to claim 1, wherein the turbulators are turbulators with 500-750 turns/m.

7. The process according to claim 1, wherein the turbulators are turbulators with 300-900 turns/m.

* * * * *